US00PP14888P2

(12) United States Plant Patent
Oudshoorn

(10) Patent No.: US PP14,888 P2
(45) Date of Patent: Jun. 8, 2004

(54) VERONICA PLANT NAMED 'EVELINE'

(50) Latin Name: *Veronica longifolia*
Varietal Denomination: Eveline

(75) Inventor: Anthonius Adrianus Maria Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 10/437,960

(22) Filed: May 13, 2003

(51) Int. Cl.[7] ..... A01H 5/00
(52) U.S. Cl. ..... Plt./251
(58) Field of Search ..... Plt./251

(56) References Cited

PUBLICATIONS http://dealtime.catalogcity.com/cc.class/cc?pcd=7809473&ccsyn=48.*

UPOV ROM GTITM Computer Database, GTI JOUVE Retrieval Software 2003/05 Citations for 'Eveline'.*

* cited by examiner

*Primary Examiner*—Bruce R. Campell
*Assistant Examiner*—W C Haas
(74) *Attorney, Agent, or Firm*—C. A. Whealy

(57) ABSTRACT

A distinct cultivar of Veronica plant named 'Eveline', characterized by its upright plant habit; freely flowering habit; and violet-colored flowers.

2 Drawing Sheets

Botanical classification/cultivar designation: *Veronica longifolia* cultivar Eveline .

BACKGROUND OF THE INVENTION

The present Invention relates to a new and distinct cultivar of Veronica plant, botanically known as *Veronica longifolia,* and hereinafter referred to by the cultivar name Eveline.

The new Veronica plant originated from a chance cross-pollination of two unidentified selections of *Veronica longifolia,* not patented. The new Veronica was discovered by the Inventor in 1998 in a controlled environment in Rijpwetering, The Netherlands. Plants of the new Veronica differed primarily from plants of the unidentified parental selections and other Veronica cultivars known to the Inventor in flower coloration.

Asexual reproduction of the new cultivar by divisions in a controlled environment in Rijpwetering, The Netherlands, has shown that the unique features of this new Veronica are stable and reproduced true to type in successive generations.

SUMMARY OF THE INVENTION

Plants of the cultivar Eveline have not been observed under all possible environmental and cultural conditions. The phenotype may vary somewhat with variations in environment such as temperature and light intensity without, however, any variance in genotype.

The following traits have been repeatedly observed and are determined to be the unique characteristics of 'Eveline'. These characteristics in combination distinguish 'Eveline' as a new and distinct cultivar.

1. Upright plant habit.
2. Freely flowering habit.
3. Violet-colored flowers.

BRIEF DESCRIPTION OF THE PHOTOGRAPHS

The accompanying colored photographs illustrate the overall appearance of the new Veronica, showing the colors as true as it is reasonably possible to obtain in colored reproductions of this type. Colors in the photographs may differ slightly from the color values cited in the detailed botanical description which accurately describe the colors of the new Veronica. The photograph on the first sheet comprises a side perspective view of a typical flowering plant of 'Eveline' grown in a container. The photograph at the top of the second sheet is a close-up view of typical inflorescences of 'Eveline'. The photograph at the bottom of the second sheet is a close-up view of typical leaves of 'Eveline'.

DETAILED BOTANICAL DESCRIPTION

In the following description, color references are made to The Royal Horticultural Society Colour Chart, 2001 Edition, except where general terms of ordinary dictionary significance are used. Plants used in the aforementioned photograph and for the following description were grown for about two years under outdoor field conditions which closely approximate commercial production conditions in Lisserbroek, The Netherlands. During the production of the plants, day temperatures ranged from 14 to 25° C. and night temperatures ranged from 4 to 16° C. The photographs and description were taken in September, 2002.

Botanical classification: *Veronica longifolia* cultivar Eveline.

Parentage: Chance cross-pollination of two unidentified selections of *Veronica longifolia,* not patented.

Propagation:

*Type.*—By divisions.

*Root description.*—Fibrous, fine; freely branching; brown in color.

Plant description:

*Form.*—Perennial flowering plant; upright plant habit; inverted triangle; moderately vigorous growth habit.

*Plant height.*—About 50 cm.

*Plant diameter.*—About 30 cm.

*Basal stem description.*—Length: About 50 cm. Diameter: About 3 mm. Internode length: About 4.4 cm. Strength: Strong. Texture: Pubescent. Color: 143A.

*Foliage description.*—Arrangement: Opposite, simple. Length: About 9 cm. Width: About 1.8 cm. Shape: Lanceolate. Apex: Acute. Base: Cuneate. Margin: Serrulate. Texture, upper and lower surfaces: Pubescent. Venation pattern: Pinnate. Color: Young foliage, upper surface: Between 137A and 139A. Young foliage, lower surface: 137B. Fully expanded foliage, upper surface: 137A. Fully expanded foliage, lower surface: 138A. Venation, upper and lower surfaces: 143C. Petioles: Length: About 1.2 cm. Diameter: About 2.5 mm. Color: 143B to 143C.

Flower description:

*Appearance.*—Single campanulate flowers with four petals; flowers arranged on terminal racemes. Flowers face mostly outwardly. Flowers not persistent.

*Quantity of flowers.*—Freely flowering habit, about 225 flowers develop per raceme.

*Natural flowering season.*—Plants flower continuously from July to late September in The Netherlands.

*Fragrance.*—None detected.

*Flower longevity.*—About seven days.

*Inflorescence length.*—About 16 cm.

*Inflorescence diameter.*—About 2.4 cm.

*Flower diameter.*—About 6 mm.

*Flower depth* (*height*).—About 9 mm.

*Flower buds.*—Length: About 5 mm. Diameter: About 2 mm. Shape: Narrowly ovoid. Color: N81A to N81B.

*Petals.*—Quantity per flower: Four; fused at the base. Arrangement: Campanulate. Length: About 6 mm. Width: About 3 mm. Shape: Narrowly spatulate. Apex: Obtuse. Base: Fused. Margin: Entire. Texture, upper and lower surface: Smooth, glabrous. Color: When opening, upper and lower surfaces: 83B. Fully opened, upper and lower surfaces: 83B.

*Sepals.*—Quantity per flower: Four, fused at base. Arrangement: Rotate. Length: About 4 mm. Width: About 1 mm. Shape: Narrowly elliptic. Apex: Acute. Base: Cuneate, fused. Margin: Entire. Texture, upper and lower surfaces: Pubescent. Color: When opening and fully opened, upper surface: 137A. When opening and fully opened, lower surface: 137C.

*Peduncles.*—Length: About 16 cm. Diameter: About 2 mm. Angle: Erect. Strength: Strong. Color: 143B.

*Pedicels.*—Length: About 2 mm. Diameter: About 0.5 mm. Angle: About 45° from vertical. Strength: Strong. Color: 143B.

*Reproductive organs.*—Stamens: Quantity per flower: Two. Anther shape: Elliptic; recurved. Anther length: About 1 mm. Anther color: N77B. Pollen amount: Scarce. Pollen color: 2C.

*Pistils.*—Quantity per flower: One. Style length: About 5 mm. Style color: N81A. Stigma shape: Ovoid. Stigma color: 143B. Ovary color: 143C.

*Fruit.*—Quantity per flower: One. Length: About 4 mm. Diameter: About 3 mm. Texture: Smooth, glabrous. Color: 152B.

*Seed.*—Length: About 1 mm. Diameter: About 1 mm. Color: N199C to N199D.

Disease/pest resistance: Plants of the new Veronica have not been noted to be resistant to pathogens or pests common to Veronica.

Temperature tolerance: Plants of the new Veronica are tolerant to temperatures from about −30 to 40° C.

It is claimed:

1. A new and distinct cultivar of Veronica plant named 'Eveline', as illustrated and described.

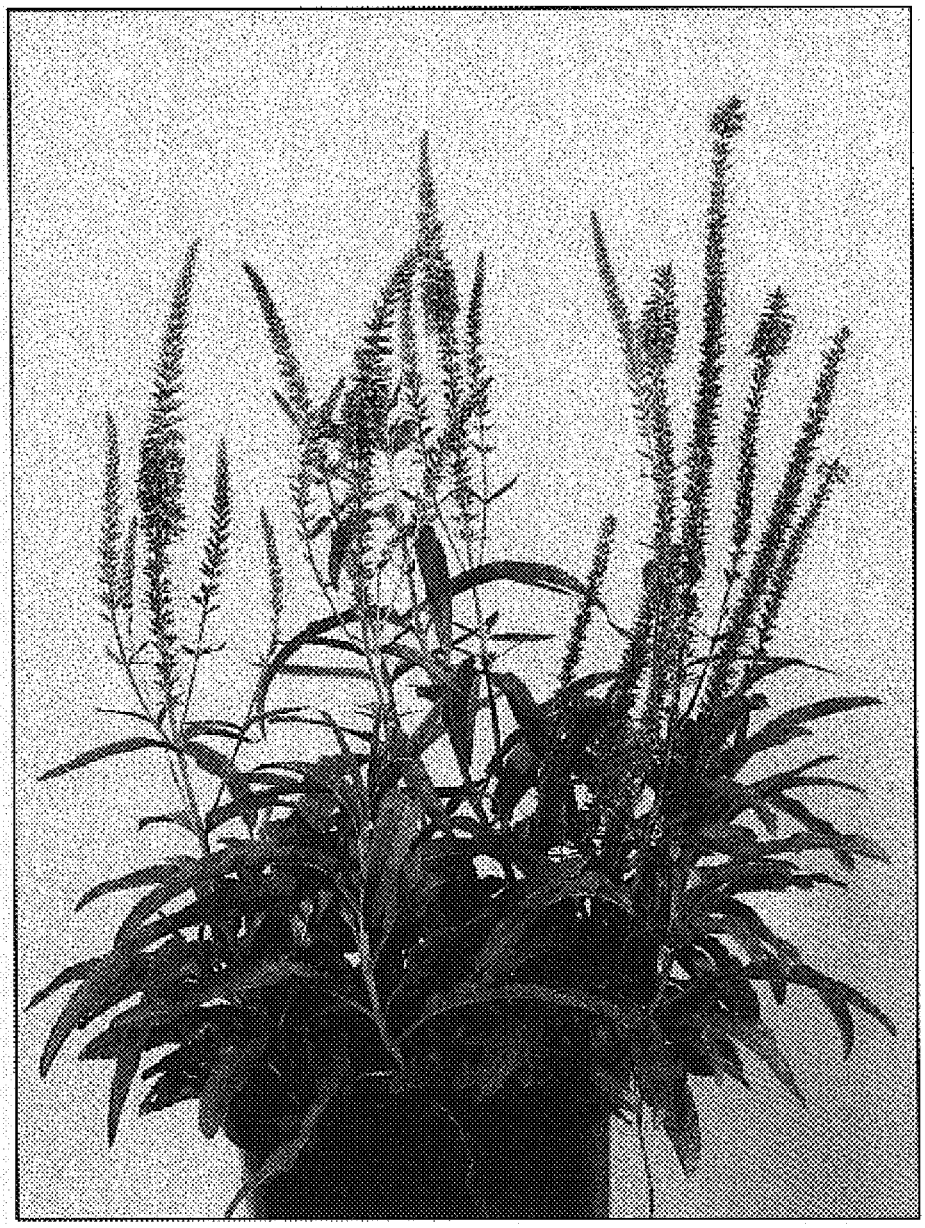

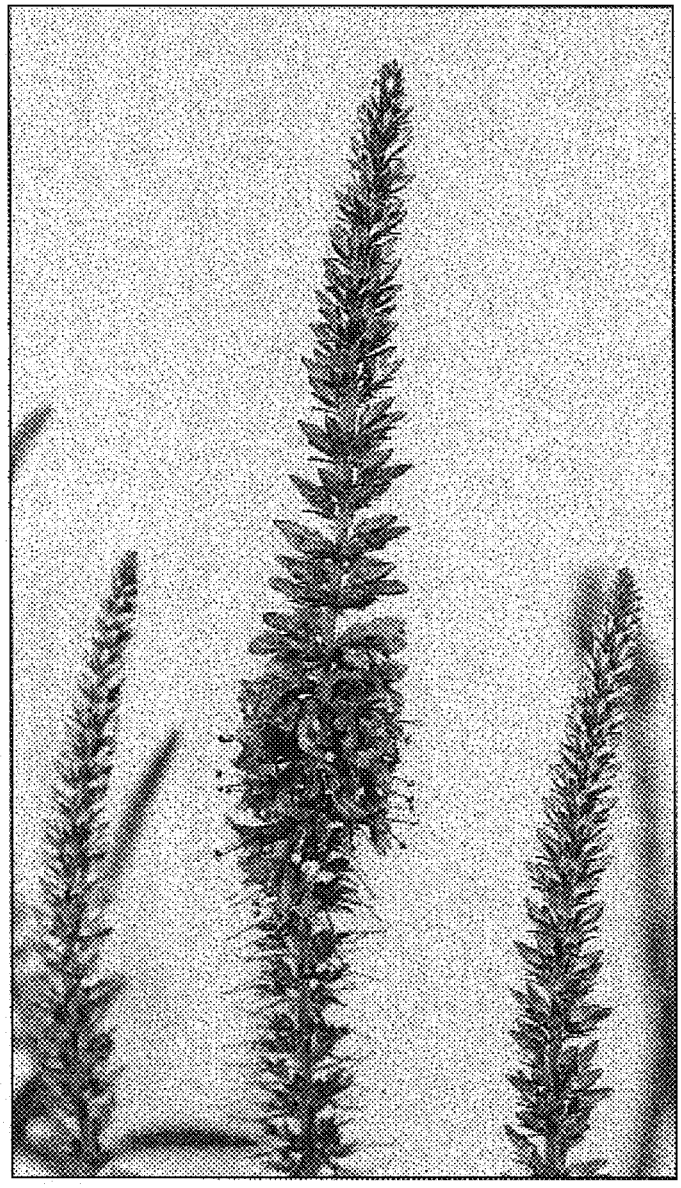
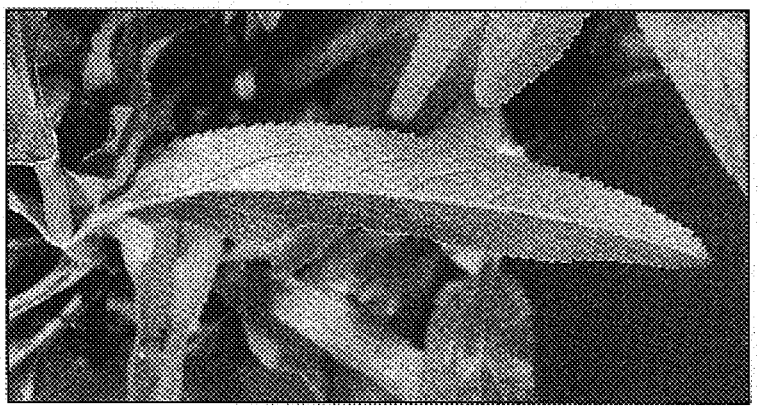

* * * * *